United States Patent
Lee et al.

(10) Patent No.: US 10,450,390 B2
(45) Date of Patent: *Oct. 22, 2019

(54) METALLOCENE COMPOUND, METALLOCENE-SUPPORTED CATALYST, AND METHOD OF PREPARING POLYOLEFIN USING THE SAME

(71) Applicant: LG CHEM, LTD., Seoul (KR)

(72) Inventors: Sung Min Lee, Daejeon (KR); Bog Ki Hong, Daejeon (KR); Kyung Jin Cho, Daejeon (KR); Se Young Kim, Daejeon (KR); Chang Woan Han, Daejeon (KR); Ki Soo Lee, Daejeon (KR); Eun Kyoung Song, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 15/507,968

(22) PCT Filed: Dec. 15, 2015

(86) PCT No.: PCT/KR2015/013734
§ 371 (c)(1),
(2) Date: Mar. 1, 2017

(87) PCT Pub. No.: WO2016/099117
PCT Pub. Date: Jun. 23, 2016

(65) Prior Publication Data
US 2017/0283522 A1 Oct. 5, 2017

(30) Foreign Application Priority Data

Dec. 15, 2014 (KR) .................. 10-2014-0180743

(51) Int. Cl.
| C08F 4/00 | (2006.01) |
|---|---|
| C08F 4/6592 | (2006.01) |
| C08F 4/652 | (2006.01) |
| C08F 10/00 | (2006.01) |
| C07C 13/465 | (2006.01) |
| C07D 221/18 | (2006.01) |
| C08F 12/00 | (2006.01) |

(52) U.S. Cl.
CPC ........ *C08F 4/65922* (2013.01); *C07C 13/465* (2013.01); *C07D 221/18* (2013.01); *C08F 4/652* (2013.01); *C08F 4/6592* (2013.01); *C08F 10/00* (2013.01); *C08F 12/00* (2013.01)

(58) Field of Classification Search
None
See application file for complete search history.

(56) References Cited

U.S. PATENT DOCUMENTS

| 5,032,562 | A | 7/1991 | Lo et al. |
|---|---|---|---|
| 5,525,678 | A | 6/1996 | Mink et al. |
| 5,886,202 | A | 3/1999 | Jung et al. |
| 5,914,289 | A | 6/1999 | Razavi |
| 6,756,455 | B2 | 6/2004 | Nagy et al. |
| 6,861,485 | B2 | 3/2005 | Wang |
| 6,967,231 | B1 | 11/2005 | Wang et al. |
| 7,189,675 | B2 | 3/2007 | Nagy |
| 7,273,914 | B2 | 9/2007 | Wang et al. |
| 7,473,745 | B2 | 1/2009 | Chandrashekar et al. |
| 8,546,595 | B2 | 10/2013 | Voskoboynikov et al. |
| 8,680,218 | B1 * | 3/2014 | Yang .................. C08F 210/16 |
| | | | 526/114 |
| 2003/0195306 | A1 | 10/2003 | Tsuie et al. |
| 2003/0229188 | A1 | 12/2003 | Nagy et al. |
| 2004/0254310 | A1 | 12/2004 | Winslow et al. |
| 2008/0293562 | A1 * | 11/2008 | Wang ..................... B01J 31/128 |
| | | | 502/117 |
| 2010/0016526 | A1 | 1/2010 | Etherton et al. |
| 2016/0159828 | A1 | 6/2016 | Lee et al. |
| 2016/0168281 | A1 | 6/2016 | Lee et al. |

FOREIGN PATENT DOCUMENTS

| JP | 06-182778 A | 7/1994 |
|---|---|---|
| JP | 09-510994 A | 11/1997 |
| JP | 2001-508486 A | 6/2001 |
| KR | 10-2004-0076965 A | 9/2004 |
| KR | 10-2005-0024287 A | 3/2005 |
| KR | 10-2006-0031633 A | 4/2006 |
| KR | 10-2015-0066344 A | 6/2015 |
| WO | 03/089485 A1 | 10/2003 |
| WO | 2004/076502 A1 | 9/2004 |
| WO | 2007/070041 A1 | 6/2007 |
| WO | WO 2007070041 A1 * | 6/2007 ............. C07F 17/00 |
| WO | 2009/032049 A1 | 3/2009 |
| WO | 2012/048067 A2 | 4/2012 |

OTHER PUBLICATIONS

Leino, et al.: "Syndiospecific Propylene Polymerization with C1 Symmetric Group 4 ansa-Metallocene Catalysts", Macromolecules, vol. 34, 2001, pp. 2072-2082.

* cited by examiner

*Primary Examiner* — Yun Qian
(74) *Attorney, Agent, or Firm* — Dentons US LLP

(57) ABSTRACT

Provided are a novel metallocene compound, a metallocene-supported catalyst, and a method of preparing a polyolefin using the same. The metallocene-supported catalyst according to the present disclosure exhibits a high polymerization activity even when the metallocene compound is supported on a support, thereby showing an excellent activity and preparing a polyolefin having a high molecular weight.

15 Claims, No Drawings

METALLOCENE COMPOUND, METALLOCENE-SUPPORTED CATALYST, AND METHOD OF PREPARING POLYOLEFIN USING THE SAME

This application is a National Stage Application of International Application No. PCT/KR2015/013734, filed on Dec. 15, 2015, which claims priority to and the benefit of priority of Korean Patent Application No. 10-2014-0180743 filed on Dec. 15, 2014, all of which are hereby incorporated by reference in their entirety for all purposes as if fully set forth herein.

BACKGROUND OF THE INVENTION

(a) Field of the Invention

The present application is based on, and claims priority from, Korean Patent Application No. 10-2014-0180743, filed on Dec. 15, 2014, the disclosure of which is hereby incorporated by reference herein in its entirety.

The present disclosure relates to a novel metallocene compound, a metallocene-supported catalyst, and a method of preparing a polyolefin using the same.

(b) Description of the Related Art

Olefin polymerization catalyst systems may be divided into Ziegler-Natta and metallocene catalysts, and these highly active catalyst systems have been developed in accordance with their characteristics. Ziegler-Natta catalyst has been widely applied to commercial processes since it was developed in the 1950's. However, since the Ziegler-Natta catalyst is a multi-active site catalyst in which a plurality of active sites are mixed, it has a feature that a resulting polymer has a broad molecular weight distribution. Also, since a compositional distribution of comonomers is not uniform, there is a problem that it is difficult to obtain desired physical properties.

Meanwhile, the metallocene catalyst includes a main catalyst having a transition metal compound as a main component and an organometallic compound cocatalyst having aluminum as a main component. Such a catalyst is a single-site catalyst which is a homogeneous complex catalyst, and offers a polymer having a narrow molecular weight distribution and a uniform compositional distribution of comonomers, depending on the single site characteristics. The stereoregularity, copolymerization characteristics, molecular weight, crystallinity, etc. of the resulting polymer may be controlled by changing a ligand structure of the catalyst and polymerization conditions.

U.S. Pat. No. 5,032,562 discloses a method of preparing a polymerization catalyst by supporting two different transition metal catalysts on one support. This catalyst is prepared by supporting a titanium (Ti)-based Ziegler-Natta catalyst which produces a high molecular weight polymer and a zirconium (Zr)-based metallocene catalyst which produces a low molecular weight polymer on one support, and results in a bimodal molecular weight distribution. This catalyst is disadvantageous in that the supporting procedure is complicated and morphology of polymers is poor due to a cocatalyst.

U.S. Pat. No. 5,525,678 discloses a method of using a catalyst system for olefin polymerization, in which a metallocene compound and a non-metallocene compound are simultaneously supported on a support to realize simultaneous polymerization of a high molecular weight polymer and a low molecular weight polymer. However, there are disadvantages that the metallocene compound and non-metallocene compound must be separately supported and the support must be pretreated with various compounds for supporting.

U.S. Pat. No. 5,914,289 discloses a method of controlling a molecular weight and a molecular weight distribution of polymers using metallocene catalysts which are respectively supported on supports. However, a large amount of solvent and a long period of time are required to prepare the supported catalysts, and a process of supporting metallocene catalysts on the respective supports is troublesome.

Korean Patent Application No. 2003-12308 discloses a method of controlling molecular weight distributions of polymers, in which the polymerization is performed while changing a combination of catalysts in a reactor by supporting a dinuclear metallocene catalyst and a mononuclear metallocene catalyst on a support together with an activating agent. However, this method has limitations in simultaneously realizing the characteristics of respective catalysts. In addition, there is a disadvantage that the metallocene catalysts are departed from a supported component of the resulting catalyst to cause fouling in the reactor.

Therefore, to solve the above drawbacks, there is a continuous demand for a method of preparing polyolefins with desired physical properties by easily preparing a hybrid supported metallocene catalyst having an excellent activity.

SUMMARY OF THE INVENTION

To solve the above problems in the prior arts, the present disclosure provides a metallocene compound which has an excellent activity and is able to prepare a polyolefin having a high molecular weight, a metallocene-supported catalyst, a method of preparing a polyolefin using the same, and a polyolefin prepared by using the same.

In particular, the present disclosure provides a metallocene compound which exhibits a high polymerization activity, even when it is supported on a support, and is able to prepare a polyolefin having a high molecular weight, a supported catalyst including the same, a method of preparing a polyolefin using the same, and a polyolefin prepared by using the same.

The present disclosure provides a metallocene compound represented by the following Chemical Formula 1:

[Chemical Formula 1]

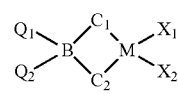

wherein M is a Group 4 transition metal;

B is carbon, silicon, or germanium;

$Q_1$ and $Q_2$ are the same as or different from each other, and each independently hydrogen, halogen, a C1 to C20 alkyl group, a C2 to C20 alkenyl group, a C6 to C20 aryl group, a C7 to C20 alkylaryl group, a C7 to C20 arylalkyl group, a C1 to C20 alkoxy group, a C2 to C20 alkoxyalkyl group, a C3 to C20 heterocycloalkyl group, or a C5 to C20 heteroaryl group;

$X_1$ and $X_2$ are the same as or different from each other, and each independently halogen, a C1 to C20 alkyl group, a C2 to C20 alkenyl group, a C6 to C20 aryl group, a nitro group, an amido group, a C1 to C20 alkylsilyl group, a C1 to C20 alkoxy group, or a C1 to C20 sulfonate group;

one of $C_1$ and $C_2$ is represented by the following Chemical Formula 2a, and the other is represented by the following Chemical Formula 2b;

[Chemical Formula 2a]

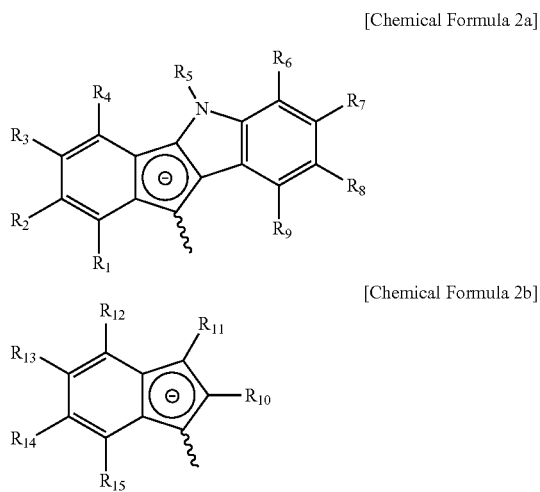

[Chemical Formula 2b]

in Chemical Formula 2a, $R_1$ to $R_9$ are the same as or different from each other, and each independently hydrogen, a C1 to C20 alkyl group, a C2 to C20 alkenyl group, a C1 to C20 alkoxy group, a C1 to C20 alkylsilyl group, a C1 to C20 silylalkyl group, a C6 to C20 aryl group, a C7 to C20 alkylaryl group, or a C7 to C20 arylalkyl group;

in Chemical Formula 2b, $R_{10}$ and $R_{12}$ to $R_{15}$ are hydrogen, $R_{11}$ is a C1 to C20 alkyl group, a C2 to C20 alkenyl group, a C1 to C20 alkylsilyl group, a C1 to C20 silylalkyl group, a C1 to C20 alkoxysilyl group, a C1 to C20 ether group, a C1 to C20 silylether group, a C1 to C20 silyloxy group, a C1 to C20 alkoxy group, a C2 to C20 alkoxyalkyl group, a C6 to C20 aryl group, a C7 to C20 alkylaryl group, or a C7 to C20 arylalkyl group.

Further, the present disclosure provides a metallocene-supported catalyst including the metallocene compound represented by Chemical Formula 1; a cocatalyst compound; and a support.

Further, the present disclosure provides a method of preparing a polyolefin, the method including polymerizing olefinic monomers in the presence of the metallocene-supported catalyst.

Further, the present disclosure provides a polyolefin which is prepared according to the above preparation method.

The metallocene-supported catalyst according to the present disclosure may be used in the preparation of polyolefins, may have an excellent activity, and may prepare a polyolefin having a high molecular weight.

Particularly, the metallocene catalyst compound of the present disclosure may exhibit a high polymerization activity even when it is supported on a support, thereby preparing a polyolefin having a high molecular weight.

Furthermore, since the catalyst has a long life-lime, its activity may be maintained even for a long residence time in a reactor.

DETAILED DESCRIPTION OF THE EMBODIMENTS

Although the terms "first", "second", etc. may be used herein to describe various elements, these terms are only used to distinguish one element from another.

Further, the terminology used herein is for the purpose of describing exemplary embodiments only and it is not intended to restrict the present invention. The singular forms are intended to include the plural forms as well, unless the context clearly indicates otherwise. The term "include", "equip", or "have" is intended to specify the presence of stated features, integers, steps, elements, or combinations thereof, but do not preclude the presence or addition of one or more other features, integers, steps, elements, or combinations thereof.

While the present invention is susceptible to various modifications and alternative forms, specific embodiments will be illustrated and described in detail as follows. It should be understood, however, that the description is not intended to limit the present invention to the particular forms disclosed, but on the contrary, the intention is to cover all modifications, equivalents, and alternatives falling within the spirit and scope of the invention.

Hereinafter, the present disclosure will be described in more detail.

The present disclosure is characterized in that a metallocene compound is represented by the following Chemical Formula 1, and a metallocene-supported catalyst includes the metallocene compound represented by the following Chemical Formula 1; a cocatalyst compound; and a support:

[Chemical Formula 1]

wherein M is a Group 4 transition metal;

B is carbon, silicon, or germanium;

$Q_1$ and $Q_2$ are the same as or different from each other, and each independently hydrogen, halogen, a C1 to C20 alkyl group, a C2 to C20 alkenyl group, a C6 to C20 aryl group, a C7 to C20 alkylaryl group, a C7 to C20 arylalkyl group, a C1 to C20 alkoxy group, a C2 to C20 alkoxyalkyl group, a C3 to C20 heterocycloalkyl group, or a C5 to C20 heteroaryl group;

$X_1$ and $X_2$ are the same as or different from each other, and each independently halogen, a C1 to C20 alkyl group, a C2 to C20 alkenyl group, a C6 to C20 aryl group, a nitro group, an amido group, a C1 to C20 alkylsilyl group, a C1 to C20 alkoxy group, or a C1 to C20 sulfonate group;

one of $C_1$ and $C_2$ is represented by the following Chemical Formula 2a, and the other is represented by the following Chemical Formula 2b;

[Chemical Formula 2a]

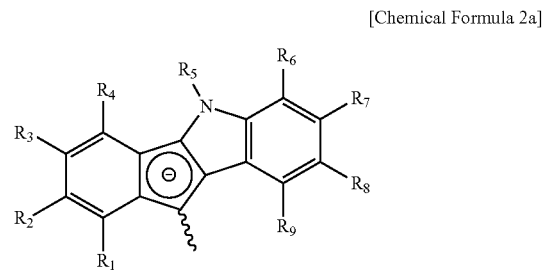

[Chemical Formula 2b]

(structure with R12, R11, R13, R10, R14, R15)

in Chemical Formula 2a, $R_1$ to $R_9$ are the same as or different from each other, and each independently hydrogen, a C1 to C20 alkyl group, a C2 to C20 alkenyl group, a C1 to C20 alkoxy group, a C1 to C20 alkylsilyl group, a C1 to C20 silylalkyl group, a C6 to C20 aryl group, a C7 to C20 alkylaryl group, or a C7 to C20 arylalkyl group;

in Chemical Formula 2b, $R_{10}$ and $R_{12}$ to $R_{15}$ are hydrogen, $R_{11}$ is a C1 to C20 alkyl group, a C2 to C20 alkenyl group, a C1 to C20 alkylsilyl group, a C1 to C20 silylalkyl group, a C1 to C20 alkoxysilyl group, a C1 to C20 ether group, a C1 to C20 silylether group, a C1 to C20 silyloxy group, a C1 to C20 alkoxy group, a C2 to C20 alkoxyalkyl group, a C6 to C20 aryl group, a C7 to C20 alkylaryl group, or a C7 to C20 arylalkyl group.

The metallocene compound may maintain an excellent activity and a polymerization property while producing a polyolefin having a high molecular weight by combination of substituents represented by Chemical Formulae 2a and 2b by applying Chemical Formula 2a having a particular substituent to one of $C_1$ and $C_2$ and applying Chemical Formula 2b to the other of $C_1$ and $C_2$ in Chemical Formula 1.

With regard to the metallocene-supported catalyst according to the present disclosure, the substituents of the metallocene compound of Chemical Formula 1 are described in more detail as follows.

The C1 to C20 alkyl group may include a linear or branched alkyl group, and specifically, it may include a methyl group, an ethyl group, a propyl group, an isopropyl group, an n-butyl group, a tert-butyl group, a pentyl group, a hexyl group, a heptyl group, an octyl group, etc., but is not limited thereto.

The C2 to C20 alkenyl group may include a linear or branched alkenyl group, and specifically, it may include an allyl group, an ethenyl group, a propenyl group, a butenyl group, a pentenyl group, etc., but is not limited thereto.

The C6 to C20 aryl group may include a single ring aryl group or a condensed ring aryl group, and specifically, it may include a phenyl group, a biphenyl group, a naphthyl group, a phenanthrenyl group, a fluorenyl group, etc., but is not limited thereto.

The C5 to C20 heteroaryl group may include a single ring heteroaryl group or a condensed ring heteroaryl group, and specifically, it may include a carbazolyl group, a pyridyl group, a quinoline group, an isoquinoline group, a thiophenyl group, a furanyl group, an imidazole group, an oxazolyl group, a thiazolyl group, a triazine group, a tetrahydropyranyl group, a tetrahydrofuranyl group, etc., but is not limited thereto.

The C1 to C20 alkoxy group may include a methoxy group, an ethoxy group, a phenyloxy group, a cyclohexyloxy group, a tert-butoxyhexyl group, etc., but is not limited thereto.

The Group 4 transition metal may include titanium, zirconium, hafnium, etc., but is not limited thereto.

With regard to the metallocene compound, $R_1$ to $R_9$ in Chemical Formula 2a are each independently hydrogen, a methyl group, an ethyl group, a propyl group, an isopropyl group, an n-butyl group, a tert-butyl group, a pentyl group, a hexyl group, a heptyl group, an octyl group, an ethylene group, a propylene group, a butenyl group, a phenyl group, a benzyl group, a naphthyl group, a methoxy group, an ethoxy group, or a tert-butoxyhexyl group, but is not limited thereto.

Further, $R_{11}$ in Chemical Formula 2b is preferably a methyl group, an ethyl group, a propyl group, an isopropyl group, an n-butyl group, a tert-butyl group, a pentyl group, a hexyl group, a heptyl group, an octyl group, an ethylene group, a propylene group, a butenyl group, a phenyl group, a benzyl group, a naphthyl group, a trimethylsilyl group, a triethylsilyl group, a tripropylsilyl group, a tributylsilyl group, a triisopropylsilyl group, a trimethylsilylmethyl group, a tert-butyldimethylsilylether group, a methoxy group, an ethoxy group, or a tert-butoxyhexyl group, but is not limited thereto.

With regard to the metallocene compound, $Q_1$ and $Q_2$ in Chemical Formula 1 are preferably a hydrogen, a methyl group, an ethyl group, a propyl group, an isopropyl group, an n-butyl group, a tert-butyl group, a methoxymethyl group, a tert-butoxymethyl group, a tert-butoxyhexyl group, a 1-ethoxyethyl group, a 1-methyl-1-methoxyethyl group, a tetrahydropyranyl group, a tetrahydrofuranyl group, and more preferably, a methyl group or a tert-butoxyhexyl group, but is not limited thereto.

Further, with regard to the metallocene compound, B in Chemical Formula 1 is preferably silicon, but is not limited thereto.

Since the metallocene compound of Chemical Formula 1 includes a structure, in which an indenoindole derivative and an indene derivative are asymmetrically crosslinked by a bridge and has an unshared electron pair which may act as a Lewis base in the ligand structure, it may show a high polymerization activity. Furthermore, the metallocene compound may prepare an olefinic polymer having a high molecular weight because nitrogen atom of the electron-rich indenoindole derivative stabilizes the beta-hydrogen of growing polymer chain by a hydrogen bond and inhibits beta-hydrogen elimination. Furthermore, since the metallocene compound includes the indene derivative having a relatively low steric hindrance, it may exhibit a high copolymerization activity and a low hydrogen reactivity, thereby polymerizing an olefin polymer having a middle or high molecular weight with a high activity.

In particular, the metallocene compound of Chemical Formula 1 has a structure, in which the substituent (R11) is placed in a specific position of the indene derivative compound of Chemical Formula 2b, and therefore, the metallocene compound may have a characteristic of excellent activity, compared to a metallocene compound including an unsubstituted indene compound or an indene compound having the substituent in any other position.

According to an embodiment of the present disclosure, a specific example of the compound represented by Chemical Formula 2a may be a compound represented by any one of the following structural formulae, but the present disclosure is not limited thereto:

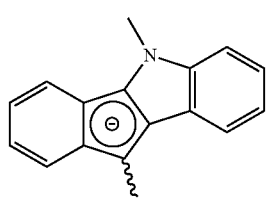

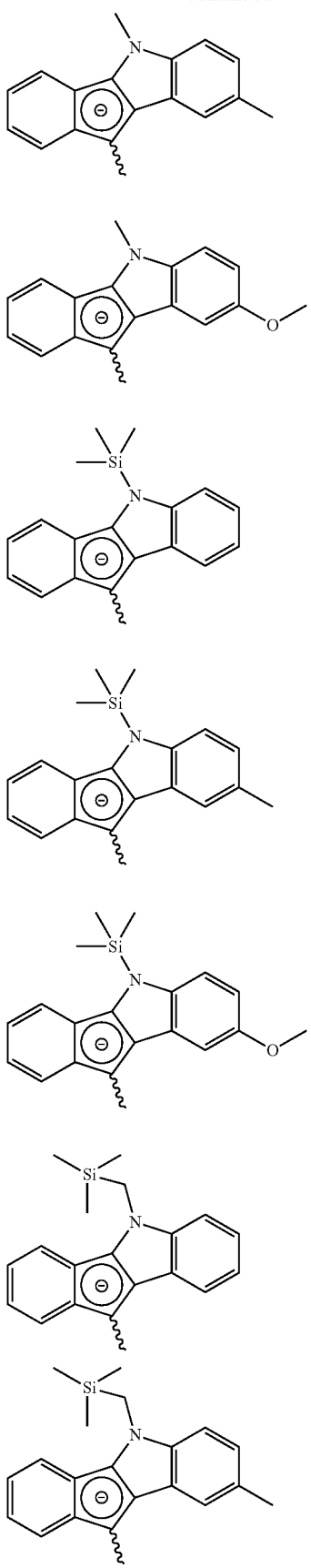
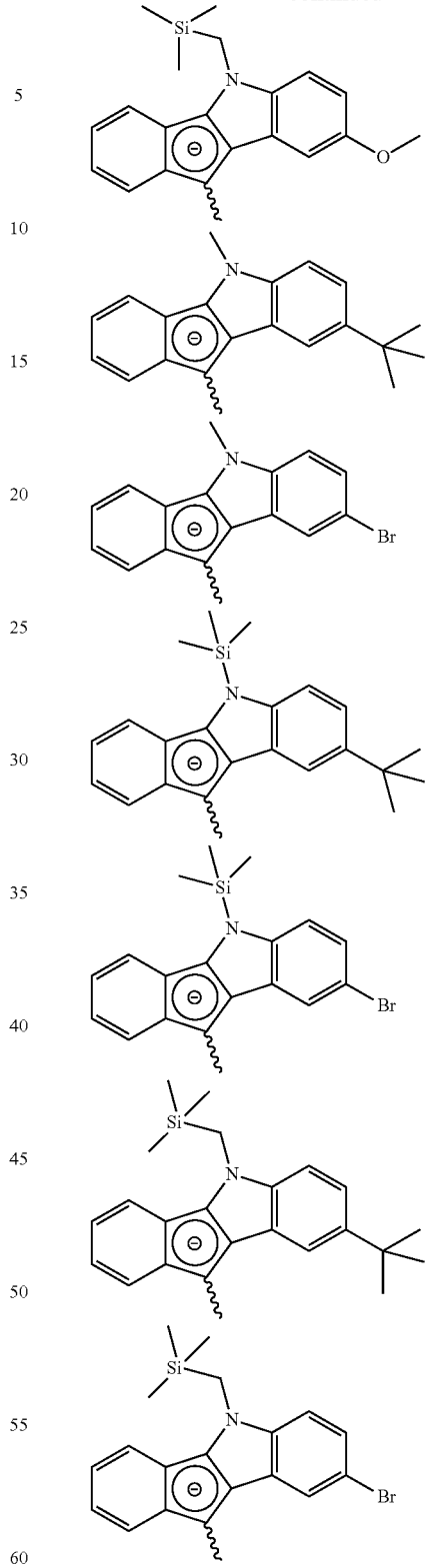
According to an embodiment of the present disclosure, a specific example f the compound represented by Chemical Formula 2b may be a compound represented by any one of the following structural formulae, but the present disclosure is not limited thereof:

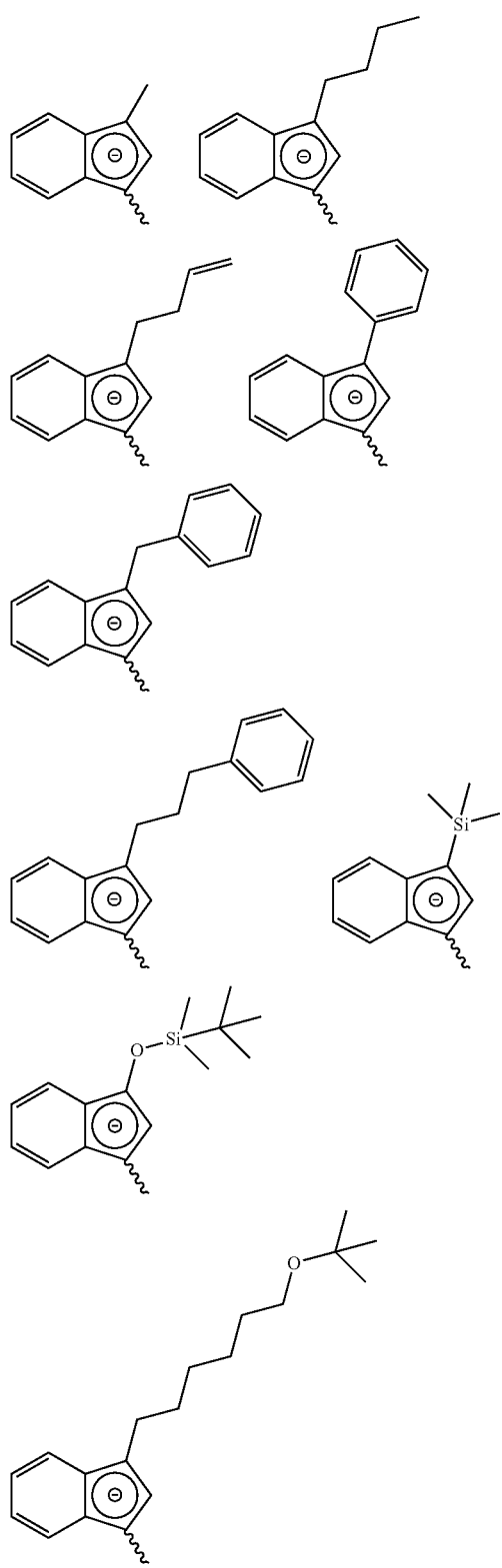
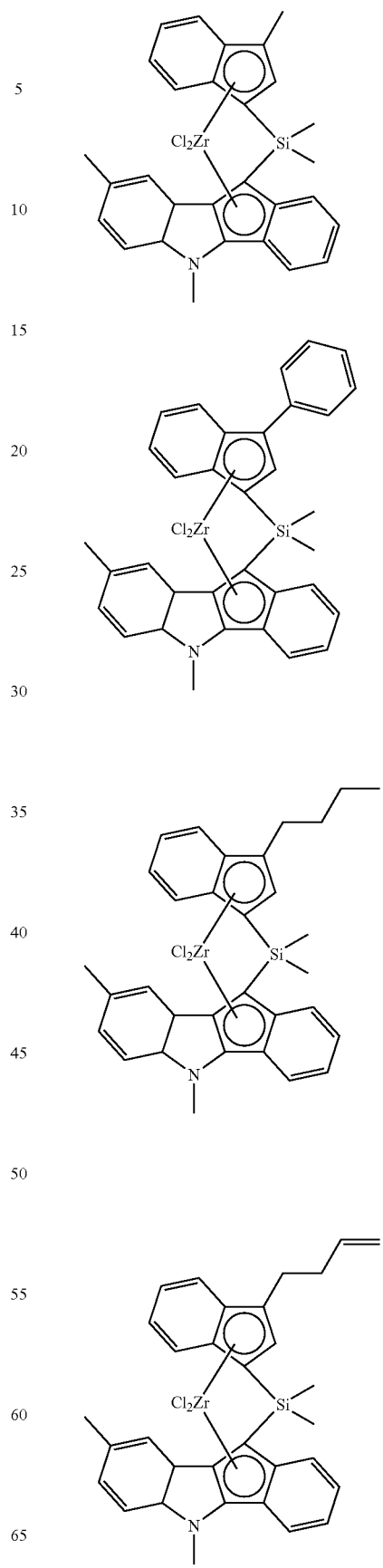
According to an embodiment of the present disclosure, a specific example f the compound represented by Chemical Formula 1 may be a compound represented by any one of the following structural formulae, but the present disclosure is not limited thereof:

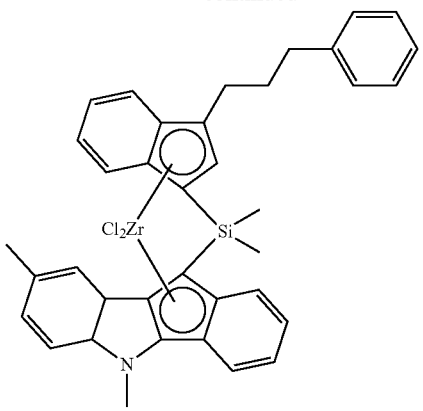
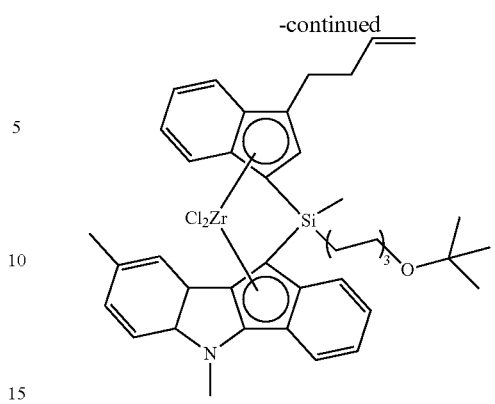

The metallocene compound may have an excellent activity and may polymerize an olefinic polymer having a middle molecular weight to a high molecular weight.

Further, the metallocene compound according to the present disclosure may polymerize an olefinic polymer having a middle or high molecular weight with still high activity even when a polymerization reaction is carried out using a supported catalyst which is prepared by supporting the metallocene compound on a support. Therefore, the metallocene compound may prepare an olefinic polymer satisfying the high molecular weight characteristic without a decrease in activity even when it is heterogeneously used with a catalyst having different characteristic, and thus the olefinic polymer having a middle or high molecular weight and a wide molecular weight distribution may be easily prepared.

The metallocene compound of Chemical Formula 1 may be obtained by connecting the indenoindole derivative and the indene derivative with a bridge compound to prepare a ligand compound, and then carrying out metallation by putting a metal precursor compound therein, but is not limited to thereto.

More specifically, for example, a lithium salt is prepared by reacting the indenoindole derivative with an organic lithium compound such as n-BuLi, and then the organic lithium salt of indenoindole is mixed and reacted with a halogenated compound of the bridge compound, and the indene derivative is reacted with the lithium salt obtained by reacting with the organic lithium compound such as n-BuLi, thereby preparing the ligand compound. The ligand compound or the lithium salt thereof is mixed with the metal precursor compound, and reacted therewith for about 12 hrs to 24 hrs until the reaction is completed, and then a reaction product is filtered and dried under reduced pressure to obtain the metallocene compound represented by Chemical Formula 1.

A method of preparing the metallocene compound will be concretely described in Examples below.

The metallocene-supported catalyst of the present disclosure may further include one or more of cocatalyst compounds represented by the following Chemical Formula 3, Chemical Formula 4, and Chemical Formula 5, in addition to the above metallocene compound:

$$—[Al(R_{16})—O]_n—$$ [Chemical Formula 3]

wherein $R_{16}$s may be the same as or different from each other, and each independently halogen; C1 to C20 hydrocarbon; or halogen-substituted C1 to C20 hydrocarbon; and n is an integer of 2 or more;

$$J(R_{17})_3$$ [Chemical Formula 4]

wherein $R_{17}$s are the same as defined in Chemical Formula 3; and

J is aluminum or boron;

   [Chemical Formula 5]

wherein E is a neutral or cationic Lewis acid;

H is a hydrogen atom;

Z is a Group 13 element; and

As may be the same as or different from each other, and each independently a C6 to C20 aryl group or a C1 to C20 alkyl group, of which one or more hydrogen atoms are unsubstituted or substituted with halogen, C1 to C20 hydrocarbon, alkoxy, or phenoxy.

Examples of the compound represented by Chemical Formula 3 may include methylaluminoxane, ethylaluminoxane, isobutylaluminoxane, butylaluminoxane, etc., and a more preferred compound is methylaluminoxane.

Examples of the compound represented by Chemical Formula 4 may include trimethylaluminum, triethylaluminum, triisobutylaluminum, tripropylaluminum, tributylaluminum, dimethylchloroaluminum, triisopropylaluminum, tri-s-butylaluminum, tricyclopentylaluminum, tripentylaluminum, triisopentylaluminum, trihexylaluminum, trioctylaluminum, ethyldimethylaluminum, methyldiethylaluminum, triphenylaluminum, tri-p-tolylaluminum, dimethylaluminummethoxide, dimethylaluminumethoxide, trimethylboron, triethylboron, triisobutylboron, tripropylboron, tributylboron, etc., and a more preferred compound is selected from trimethylaluminum, triethylaluminum, and triisobutylaluminum.

Examples of the compound represented by Chemical Formula 5 may include triethylammonium tetraphenylboron, tributylammonium tetraphenylboron, trimethylammonium tetraphenylboron, tripropylammonium tetraphenylboron, trimethylammonium tetra(p-tolyl)boron, trimethylammonium tetra(o,p-dimethylphenyl)boron, tributylammonium tetra(p-trifluoromethylphenyl)boron, trimethylammonium tetra(p-trifluoromethylphenyl)boron, tributylammonium tetrapentafluorophenylboron, N,N-diethylanilinium tetraphenylboron, N,N-diethylanilinium tetrapentafluorophenylboron, diethylammonium tetrapentafluorophenylboron, triphenylphosphonium tetraphenylboron, trimethylphosphonium tetraphenylboron, triethylammonium tetraphenylaluminum, tributylammonium tetraphenylaluminum, trimethylammonium tetraphenylaluminum, tripropylammonium tetraphenylaluminum, trimethylammonium tetra(p-tolyl)aluminum, tripropylammonium tetra(p-tolyl)aluminum, triethylammonium tetra(o,p-dimethylphenyl)aluminum, tributylammonium tetra(p-trifluoromethylphenyl)aluminum, trimethylammonium tetra(p-trifluoromethylphenyl)aluminum, tributylammonium tetrapentafluorophenylaluminum, N,N-diethylanilinium tetraphenylaluminum, N,N-diethylanilinium tetrapentafluorophenylaluminum, diethylammonium tetrapentatetraphenylaluminum, triphenylphosphonium tetraphenylaluminum, trimethylphosphonium tetraphenylaluminum, tripropylammonium tetra(p-tolyl)boron, triethylammonium tetra(o,p-dimethylphenyl)boron, tributylammonium tetra(p-trifluoromethylphenyl)boron, triphenylcarboniumtetra(p-trifluoromethylphenyl)boron, triphenylcarboniumtetrapentafluorophenylboron, etc.

Preferably, alumoxane may be used, and more preferably, methylalumoxane (MAO), an alkyl alumoxane, may be used.

The metallocene-supported catalyst according to the present disclosure may be prepared by a first method including 1) contacting the metallocene compound represented by Chemical Formula 1 with the compound represented by Chemical Formula 3 or Chemical Formula 4 to obtain a mixture; and 2) adding the compound represented by Chemical Formula 5 to the mixture.

Furthermore, the metallocene-supported catalyst according to the present disclosure may be prepared by a second method of contacting the metallocene compound represented by Chemical Formula 1 with the compound represented by Chemical Formula 3.

In the first method of preparing the supported catalyst, a molar ratio of the metallocene compound represented by Chemical Formula 1/the compound represented by Chemical Formula 3 or Chemical Formula 4 is preferably 1/5,000 to 1/2, more preferably 1/1,000 to 1/10, and most preferably 1/500 to 1/20. When the molar ratio of the metallocene compound represented by Chemical Formula 1/the compound represented by Chemical Formula 3 or Chemical Formula 4 exceeds 1/2, there is a problem that the alkylating agent is very small in quantity and the metal compound is not completely alkylated, and when the molar ratio is less than 1/5,000, the alkylation of the metal compound is accomplished, but there is a problem that the alkylated metal compound is not completely activated due to a side reaction between the remaining excess alkylating agent and an activator of Chemical Formula 6.

Furthermore, a molar ratio of the metallocene compound represented by Chemical Formula 1/the compound represented by Chemical Formula 5 is preferably 1/25 to 1, more preferably 1/10 to 1, and most preferably 1/5 to 1. When the molar ratio of the metallocene compound represented by Chemical Formula 1/the compound represented by Chemical Formula 5 exceeds 1, there is a problem that the activity of the prepared supported catalyst is deteriorated because the activator is relatively small in quantity and the metal compound is not completely activated, and when the molar ratio is less than 1/25, the activation of the metal compound is completely accomplished, but there is a problem that cost of the supported catalyst is not economical or purity of the polymer to be prepared is decreased due to the remaining excess activator.

In the second method of preparing the supported catalyst, a molar ratio of the metallocene compound represented by Chemical Formula 1/the compound represented by Chemical Formula 3 is preferably 1/10,000 to 1/10, more preferably 1/5,000 to 1/100, and most preferably 1/3,000 to 1/500. When the molar ratio exceeds 1/10, there is a problem that the activity of the prepared supported catalyst is deteriorated because the activator is relatively small in quantity and the metal compound is not completely activated, and when the molar ratio is less than 1/10,000, the activation of the metal compound is completely accomplished, but there is a problem that cost of the supported catalyst is not economical or purity of the polymer to be prepared is decreased due to the remaining excess activator.

As a reaction solvent used for preparing the supported catalyst, a hydrocarbon solvent such as pentane, hexane, heptane, etc., or an aromatic solvent such as benzene, toluene, etc. may be used.

Furthermore, the supported catalyst may include the metallocene compound and the cocatalyst compound in the form of being supported on a support.

When the metallocene compound and the cocatalyst compound are used in the form of being supported on a support, the metallocene compound may be included in an amount of about 0.5 parts by weight to about 20 parts by weight and the cocatalyst may be included in an amount of about 1 part by weight to about 1,000 parts by weight, based on 100 parts by weight of the support. Preferably, the metallocene compound may be included in an amount of about 1 part by weight to about 15 parts by weight and the cocatalyst may be included in an amount of about 10 parts by weight to about 500 parts by weight, based on 100 parts by weight of the support. Most preferably, the metallocene compound may be included in an amount of about 1 part by weight to about 100 parts by weight and the cocatalyst may be included in an amount of about 40 parts by weight to about 150 parts by weight, based 100 parts by weight of the support.

In the metallocene-supported catalyst of the present disclosure, a weight ratio of the total transition metals included in the metallocene compound to the support may be 1:10 to 1:1,000. When the support and the metallocene compound are included at the above weight ratio, an optimal shape may be obtained. Further, a weight ratio of the cocatalyst compound to the support may be 1:1 to 1:100. When the cocatalyst and the metallocene compound are included at the above weight ratio, activity and a microstructure of the polymer may be optimized.

Meanwhile, as long as the support is a metal, a metal salt, or a metal oxide which is commonly used in supported catalysts, there is no limitation in the constitution. Specifically, it may include any support selected from the group consisting of silica, silica-alumina, and silica-magnesia. The support may be dried at a high temperature. Generally, the support may include an oxide, a carbonate, a sulfate, or a nitrate of a metal, such as $Na_2O$, $K_2CO_3$, $BaSO_4$ and $Mg(NO_3)_2$, etc.

An amount of hydroxy groups (—OH) on the surface of the support is preferably as small as possible, but it is practically difficult to eliminate all hydroxy groups. The amount of hydroxy groups may be controlled by the preparation method, the preparation conditions, the drying conditions (temperature, time, drying method, etc.), etc. of the support, and the amount is preferably 0.1 mmol/g to 10 mmol/g, more preferably 0.1 mmol/g to 1 mmol/g, and much more preferably 0.1 mmol/g to 0.5 mmol/g. In order to reduce the side-reaction by a few hydroxy groups remaining after drying, a support from which hydroxy groups are chemically eliminated while preserving highly reactive siloxane groups that participate in supporting may be used.

The metallocene-supported catalyst according to the present disclosure may be used as it is in polymerization of olefinic monomers. Also, the metallocene-supported catalyst according to the present disclosure may be prepared as a pre-polymerized catalyst by contacting the catalyst with an olefinic monomer. For example, it may be prepared as a pre-polymerized catalyst by contacting the catalyst with an olefinic monomer such as ethylene, propylene, 1-butene, 1-hexene, 1-octene, etc.

The metallocene-supported catalyst according to the present disclosure is prepared, for example, by supporting the cocatalyst compound on the support; and supporting the metallocene compound represented by Chemical Formula 1 on the support. Between the respective supporting steps, washing may be further carried out by using a solvent.

The process of preparing the metallocene-supported catalyst as above may be carried out at a temperature of about 0° C. to about 100° C. under a normal pressure, but is not limited thereto.

Meanwhile, the present disclosure provides a method of preparing a polyolefin by polymerizing olefinic monomers in the presence of the metallocene-supported catalyst, and a polyolefin prepared by the above preparation method.

The olefinic monomer may include ethylene, alpha-olefin, cyclic olefin, diene olefin or triene olefin having two or more double bonds.

Specific examples of the olefinic monomer may include ethylene, propylene, 1-butene, 1-pentene, 4-methyl-1-pentene, 1-hexene, 1-heptene, 1-octene, 1-decene, 1-undecene, 1-dodecene, 1-tetradecene, 1-hexadecene, 1-eicosene, norbornene, norbornadiene, ethylidenenorbornene, phenylnorbornene, vinylnorbornene, dicyclopentadiene, 1,4-butadiene, 1,5-pentadiene, 1,6-hexadiene, styrene, alpha-methylstyrene, divinylbenzene, 3-chloromethylstyrene, etc., and these monomers may be copolymerized by mixing two or more thereof.

The polymerization reaction may be carried out by homopolymerizing one type of olefinic monomer or copolymerizing two or more types of monomers, using a continuous slurry polymerization reactor, a loop slurry reactor, a gas phase reactor, or a solution reactor.

The metallocene-supported catalyst may be used after being dissolved or diluted in an aliphatic hydrocarbon solvent having 5 to 12 carbon atoms, for example, pentane, hexane, heptane, nonane, decane, and isomers thereof, an aromatic hydrocarbon solvent such as toluene and benzene, or a hydrocarbon solvent substituted with a chlorine atom such as dichloromethane and chlorobenzene. It is preferable that the solvent is used, after a small amount of water, air or the like acting as a catalyst poison is removed by treating with a small amount of alkyl aluminum. It is also possible to perform using an additional cocatalyst.

The polymerization of the olefinic monomer may be carried out at a temperature of about 25° C. to about 500° C. and a pressure of about 1 $kgf/cm^2$ to about 100 $kgf/cm^2$ for about 1 hr to about 24 hrs. Specifically, the polymerization of the olefinic monomer may be carried out at a temperature of about 25° C. to about 500° C., preferably about 25° C. to about 200° C., and more preferably about 50° C. to about 100° C. Furthermore, the reaction pressure may be about 1 $kgf/cm^2$ to about 100 $kgf/cm^2$, preferably about 1 $kgf/cm^2$ to about 50 $kgf/cm^2$, and more preferably about 5 $kgf/cm^2$ to about 40 $kgf/cm^2$.

In the polyolefin prepared according to the present disclosure, specific examples of the olefinic monomer may include ethylene, propylene, 1-butene, 1-pentene, 4-methyl-1-pentene, 1-hexene, 1-heptene, 1-octene, 1-decene, 1-undecene, 1-dodecene, 1-tetradecene, 1-hexadecene, 1-eicosene, etc., and it may be also a copolymer obtained by copolymerizing two or more thereof.

The polyolefin may be a polyethylene polymer, but is not limited thereto.

In the case where the polyolefin is an ethylene/alpha-olefin copolymer, a content of alpha-olefin as a comonomer is not particularly limited, and it may be adequately selected according to the use or purpose of the polyolefin. More specifically, the content may be more than 0 mole % and 99 mole % or less.

For example, the polyolefin prepared by using the metallocene-supported catalyst of the present disclosure may exhibit a high molecular weight. When the polyolefin is prepared by using the supported catalyst, in which the metallocene compound is supported on the support, a high-molecular-weight polyolefin having a weight average molecular weight of about 200,000 g/mol or more, for example, about 200,000 g/mol to about 900,000 g/mol, or about 400,000 g/mol to about 900,000 g/mol may be prepared.

Further, the metallocene-supported catalyst of the present disclosure exhibits an excellent activity, and the polyolefin prepared by using the metallocene-supported catalyst of the present disclosure exhibits a wide molecular weight distribution (PDI) of about 2.0 to about 5.0, or about 2.0 to about 4.0, or about 2.0 to about 3.0, thereby showing excellent processability.

Further, according to an embodiment of the present disclosure, the polyolefin may have a density of about 0.85 g/cm³ to about 0.96 g/cm³, and preferably, about 0.90 g/cm³ to about 0.95 g/cm³.

Hereinafter, preferred Examples are provided for better understanding of the present disclosure. However, the following Examples are provided for illustrative purposes only and the present disclosure is not intended to be limited by these Examples.

EXAMPLE

<Preparation Example of Metallocene Compound>

Preparation Example 1

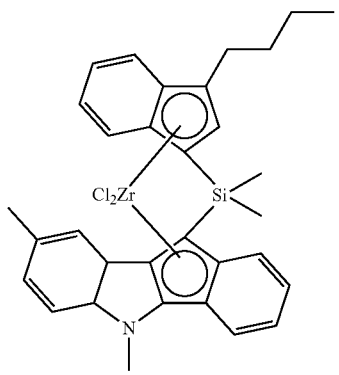

1-1 Preparation of Ligand Compound 1.73 g (10 mmol) of indenoindole was injected into a 250 mL dried Schlenk flask and 40 mL of ether was added under reduced pressure. After the ether solution was cooled down to 0° C., the atmosphere in the flask was replaced by argon and 4.8 mL (12 mmol) of 2.5 M n-BuLi hexane solution was slowly added dropwise thereto. The reaction mixture was gradually raised to room temperature, and stirred until the next day. 20 mL of ether was injected into another 250 mL Schlenk flask, and 3.6 mL (30 mmol) of dichlorodimethylsilane was added thereto. After the flask was cooled down to −78° C., a lithiated solution of indenoindole was injected thereto via a cannula. The completely injected mixture was gradually raised up to room temperature, and then stirred for about 5 hours. The ether used as a solvent and the remaining excessive dichlorodimethylsilane were removed under vacuum/reduced pressure. A resulting product was confirmed by NMR, and 10-(chlorodimethylsilyl)-5,8-dimethyl-5,10-dihydroindeno[1,2-b]indole with purity of about 95% or more was obtained.

After confirming synthesis of the indenoindole part, 1.72 g (10 mmol) of buthylindene was injected into a 100 mL dried Schlenk flask and dissolved in 40 mL of ether. Thereafter, 4.8 mL (12 mmol) of 2.5 M n-BuLi hexane solution was slowly added dropwise thereto at −78° C., and stirred for one day. The fluorene part previously synthesized was dissolved in 40 mL of ether, and then a lithiated solution of buthylindene was added dropwise at −78° C. About 20 hrs later, quenching was carried out by adding 50 ml of water to the flask, and an organic layer was separated and dried over MgSO₄. From a mixture obtained by filtration, the solvent was evaporated under vacuum/reduced pressure. As a result, 4.7 g (10.2 mmol, 102%) of brown oil was obtained.

¹H NMR (500 MHz, CDCl₃): 0.03 (3H, d), 0.23 (3H, d), 1.67 (2H, m), 2.90 (3H, d), 3.13 (2H, m), 4.12 (1H, s), 4.47 (1H, s), 4.54 (3H, d), 5.47 (1H, m), 5.57 (1H, m), 6.49 (1H, m), 6.50, 6.73 (1H, d), 7.65 (2H, m), 7.67~8.03 (6H, m), 8.23 (2H, m)

1-2 Preparation of Metallocene Compound

A ligand was added to a 250 mL Schlenk flask dried in an oven, and dissolved in ether, and then 2.5 equivalent weights of n-BuLi solution was added, followed by lithiation until the next day. 1 equivalent weight of ZrCl₄(THF)₂ was taken in a glove box, and injected into a 250 mL Schlenk flask to which ether or toluene was added to prepare a suspension. The above two flasks were cooled down to −78° C., and then ligand anion was slowly added to the Zr suspension. After completion of the injection, the reaction mixture was slowly warmed up to room temperature. In this process, when successful metallation was achieved, a purple color unique to the catalyst precursor was observed. The mixture was stirred overnight and then toluene or ether in the mixture was removed to a volume of about 1/5 under vacuum/reduced pressure, and hexane of about 5 times volume of the remaining solvent was added thereto. In this regard, the reason for adding hexane is to promote crystallization because the synthesized catalyst precursor is less soluble in hexane. This hexane slurry was filtered under argon atmosphere, and a filtered solid and a filtrate were evaporated under vacuum/reduced pressure. The resulting filter cake was weighed in a glove box and sampled to identify the synthesis, yield and purity. As a metallation solvent, ether was used, and 2.4 g (73.5%) of a violet solid was obtained from 4.7 g (10.2 mmol) of the ligand.

Purity based on NMR (wt %)=73.5%. Mw=621.83.

¹H NMR (500 MHz, CDCl₃): 0.72 (3H, m), 0.82 (2H, m), 1.19 (2H, m), 1.23, 1.35 (3H, s), 1.49, 1.57 (3H, s), 2.54 (3H, s), 3.52, 3.84 (2H, m), 3.95, 4.16 (3H, s), 5.62 (1H, s), 7.02 (2H, m), 7.22~7.61 (8H, m), 7.82 (2H, m)

Preparation Example 2

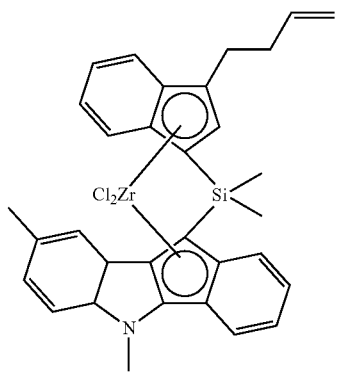

2-1 Preparation of Ligand Compound 1.73 g (10 mmol) of indenoindole was injected into a 250 mL dried Schlenk flask and 40 mL of ether was added under reduced pressure. After the ether solution was cooled down to 0° C., the atmosphere in the flask was replaced by argon and 4.8 mL (12 mmol) of 2.5 M n-BuLi hexane solution was slowly added dropwise thereto. The reaction mixture was gradually raised to room temperature, and stirred until the next day. 20 mL of ether was injected into another 250 mL Schlenk flask, and 3.6 mL (30 mmol) of dichlorodimethylsilane was added thereto. After the flask was cooled down to −78° C., a lithiated solution of indenoindole was injected thereto via a cannula. The completely injected mixture was gradually raised up to room temperature, and then stirred for about 5 hours. The ether used as a solvent and the remaining excessive dichlorodimethylsilane were removed under vacuum/reduced pressure. A resulting product was confirmed by NMR, and 10-(chlorodimethylsilyl)-5,8-dimethyl-5,10-dihydroindeno[1,2-b]indole with purity of about 95% or more was obtained.

After confirming synthesis of the indenoindole part, 1.7 g (10 mmol) of 3-(but-3-enyl)-1H-indene was injected into a 100 mL dried Schlenk flask and dissolved in 40 mL of ether. Thereafter, 4.8 mL (12 mmol) of 2.5 M n-BuLi hexane solution was slowly added dropwise thereto at −78° C., and stirred for one day. The fluorene part previously synthesized was dissolved in 40 mL of ether, and then a lithiated solution of buthylindene was added dropwise at −78° C. About 20 hrs later, quenching was carried out by adding 50 ml of water to the flask, and an organic layer was separated and dried over MgSO$_4$. From a mixture obtained by filtration, the solvent was evaporated under vacuum/reduced pressure. As a result, 4.4 g (9.7 mmol, 96.7%) of violet oil was obtained.

$^1$H NMR (500 MHz, CDCl3): 0.03 (3H, d), 0.23 (3H, d), 1.67 (2H, m), 2.90 (3H, d), 3.13 (2H, m), 4.12 (1H, s), 4.47 (1H, s), 4.54 (3H, d), 5.47 (1H, m), 5.57 (1H, m), 6.49 (1H, m), 6.50, 6.73 (1H, d), 7.65 (2H, m), 7.67~8.03 (6H, m), 8.23 (2H, m)

2-2 Preparation of Metallocene Compound

A ligand was added to a 250 mL Schlenk flask dried in an oven, and dissolved in ether, and then 2.5 equivalent weights of n-BuLi solution was added, followed by lithiation until the next day. 1 equivalent weight of ZrCl$_4$(THF)$_2$ was taken in a glove box, and injected into a 250 mL Schlenk flask to which ether or toluene was added to prepare a suspension. The above two flasks were cooled down to −78° C., and then ligand anion was slowly added to the Zr suspension. After completion of the injection, the reaction mixture was slowly warmed up to room temperature. In this process, when successful metallation was achieved, a purple color unique to the catalyst precursor was observed. The mixture was stirred overnight and then toluene or ether in the mixture was removed to a volume of about 1/5 under vacuum/reduced pressure, and hexane of about 5 times volume of the remaining solvent was added thereto. In this regard, the reason for adding hexane is to promote crystallization because the synthesized catalyst precursor is less soluble in hexane. This hexane slurry was filtered under argon atmosphere, and a filtered solid and a filtrate were evaporated under vacuum/reduced pressure. The resulting filter cake was weighed in a glove box and sampled to identify the synthesis, yield and purity. As a metallation solvent, ether was used, and 4.0 g (66.6%) of a violet solid was obtained from 4.4 g (9.7 mmol) of the ligand.

Purity based on NMR (wt %)=83.1%. Mw=619.81.

$^1$H NMR (500 MHz, CDCl$_3$): 1.24, 1.36 (3H, s), 1.51, 1.58 (3H, s), 1.68, 1.87 (1H, m), 2.46, 2.56 (1H, m), 2.82 (1H, m), 3.85 (1H, m), 3.95, 4.16 (3H, s), 4.84 (1H, m), 5.56 (1H, m), 6.55 (1H, m), 6.98 (2H, m), 7.00~7.33 (3H, m), 7.42 (2H, m), 7.53 (2H, m), 7.61 (2H, d), 7.84 (2H, m)

Preparation Example 3

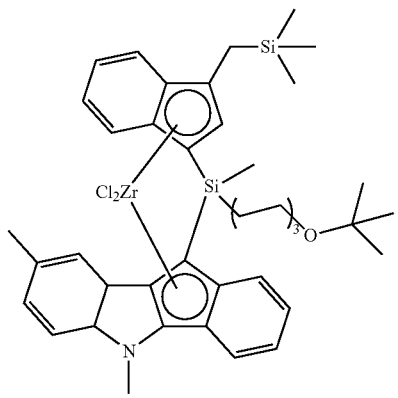

3-1 Preparation of Ligand Compound 2.331 g (10 mmol) of indenoindole was injected into a 250 mL dried Schlenk flask and 40 mL of ether was added under argon atmosphere. After the ether solution was cooled down to 0° C., 4.8 mL (12 mmol) of 2.5 M n-BuLi hexane solution was slowly added dropwise thereto. The reaction mixture was gradually raised to room temperature, and stirred until the next day. 20 mL of ether was injected into another 250 mL Schlenk flask, and 3.6 mL (30 mmol) of dichloromethyl(tertbutoxyhexyl)silane was added thereto. After the flask was cooled down to −78° C., a lithiated solution of indenoindole was injected thereto via a cannula. The completely injected mixture was gradually raised up to room temperature, stirred for about 5 hours, and then stirred for one day. Quenching was carried out by adding 50 ml of water to the flask, and an organic layer was separated and dried over MgSO$_4$. The ether used as a solvent was removed under reduced pressure. A resulting product was confirmed by NMR, and 10-((6-(tert-butoxy)hexyl)chloro(methyl)silyl)-5,8-dimethyl-5,10-dihydroindeno[1,2-b]indole with purity of about 95% or more was obtained.

After confirming synthesis of the indenoindole part, 1.7 g (10 mmol) of ((1H-inden-3-yl)methyl)trimethylsilane was injected into a 100 mL dried Schlenk flask and dissolved in 40 mL of ether. Thereafter, 4.8 mL (12 mmol) of 2.5 M n-BuLi hexane solution was slowly added dropwise thereto at −78° C., and stirred for one day. 10-((6-(tert-butoxy)hexyl)chloro(methyl)silyl)-5,8-dimethyl-5,10-dihydroindeno[1,2-b]indole previously synthesized was dissolved in 40 mL of ether, and then a lithiated solution of ((1H-inden-3-yl)methyl)trimethylsilane was added dropwise at −78° C. About 20 hrs later, quenching was carried out by adding 50 ml of water to the flask, and an organic layer was separated and dried over MgSO$_4$. From a mixture obtained by filtration, the solvent was evaporated under vacuum/reduced pressure. As a result, 6.5 g (10.2 mmol, 100%) of yellow oil of 10-((6-(tert-butoxy)hexyl)(methyl)(3-((trimethylsilyl)methyl)-1H-inden-1-yl)silyl)-5,8-dimethyl-5,10-dihydroindeno[1,2-b]indo was obtained.

Mw: 634.05, Purity (wt %)=100%

$^1$H NMR (500 MHz, CDCl3): −0.40, −0.37 (3H, d), 0.017 (9H, m), 1.10 (4H, m), 1.18 (9H, s), 1.34 (6H, m), 2.41 (3H, m), 3.25 (2H, m), 3.25 (1H, m), 3.53 (1H, m), 4.09 (3H, s), 5.62, 5.82, 5.95, 5.95, 6.11 (1H, s), 7.04~7.32 (9H, m), 7.54 (1H, m), 7.75 (1H, m).

3-2 Preparation of Metallocene Compound

A ligand was added to a 250 mL Schlenk flask dried in an oven, and dissolved in ether, and then 2.1 equivalent weights of n-BuLi solution was added, followed by lithiation until the next day. 1 equivalent weight of $ZrCl_4(THF)_2$ was taken in a glove box, and injected into a 250 mL Schlenk flask to which ether or toluene was added to prepare a suspension. The above two flasks were cooled down to −78° C., and then ligand anion was slowly added to the Zr suspension. After completion of the injection, the reaction mixture was slowly warmed up to room temperature. In this process, when successful metallation was achieved, a purple color unique to the catalyst precursor was observed. The mixture was stirred overnight and then toluene or ether in the mixture was removed to a volume of about 1/5 under vacuum/reduced pressure, and hexane of about 5 times volume of the remaining solvent was added thereto. In this regard, the reason for adding hexane is to promote crystallization because the synthesized catalyst precursor is less soluble in hexane. This hexane slurry was filtered under argon atmosphere, and a filtered solid and a filtrate were evaporated under vacuum/reduced pressure. The resulting filter cake was weighed in a glove box and sampled to identify the synthesis, yield and purity. As a metallation solvent, ether was used, and 6.08 g (76.5%) of a violet solid was obtained from 6.4 g (10 mmol) of the ligand.

Purity based on NMR (wt %)=100%. Mw=794.17.

$^1$H NMR (500 MHz, $CDCl_3$): −0.23, −0.16 (9H, d), 0.81 (3H, m), 1.17 (9H, m), 1.20~1.24 (3H, m), 1.31 (2H, s), 1.62~1.74 (5H, m), 1.99~2.11 (2H, m), 2.55 (3H, d), 3.33 (2H, m), 3.95, 4.13 (3H, s), 5.17, 5.21, 5.32 (1H, s), 6.89~7.07 (3H, m), 7.12~7.21 (3H, m), 7.29 (1H, m), 7.36 (1H, m), 7.44 (1H, m), 7.84 (1H, m).

Preparation Example 4

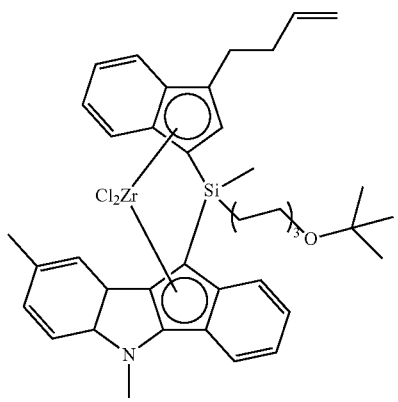

4-1 Preparation of Ligand Compound

Indenoindole was injected under argon atmosphere and 40 mL of ether was injected. After the ether solution was cooled down to 0° C., 4.8 mL (12 mmol) of 2.5 M n-BuLi hexane solution was slowly added dropwise thereto. The reaction mixture was gradually raised to room temperature, and stirred until the next day. 20 mL of ether was injected into another 250 mL Schlenk flask, and 3.6 mL (30 mmol) of dichloromethyl(tertbutoxyhexyl)silane was added thereto. After the flask was cooled down to −78° C., a lithiated solution of indenoindole was injected thereto via a cannula. The completely injected mixture was gradually raised up to room temperature, stirred for about 5 hours, and then stirred for one day. Quenching was carried out by adding 50 ml of water to the flask, and an organic layer was separated and dried over $MgSO_4$. The ether used as a solvent was removed under reduced pressure. A resulting product was confirmed by NMR, and 10-((6-(tert-butoxy)hexyl)chloro(methyl)silyl)-5,8-dimethyl-5,10-dihydroindeno[1,2-b]indole with purity of about 95% or more was obtained.

After confirming synthesis of the indenoindole part, 1.7 g (10 mmol) of 3-(but-3-en-1-yl)-1H-indene was injected into a 100 mL dried Schlenk flask and dissolved in 40 mL of ether. Thereafter, 4.8 mL (12 mmol) of 2.5 M n-BuLi hexane solution was slowly added dropwise thereto at −78° C., and stirred for one day. 10-((6-(tert-butoxy)hexyl)chloro(methyl)silyl)-5,8-dimethyl-5,10-dihydroindeno[1,2-b]indole previously synthesized was dissolved in 40 mL of ether, and then a lithiated solution of buthylindene was added dropwise at −78° C. About 20 hrs later, quenching was carried out by adding 50 ml of water to the flask, and an organic layer was separated and dried over $MgSO_4$. From a mixture obtained by filtration, the solvent was evaporated under vacuum/reduced pressure. As a result, 5.8 g (9.7 mmol, 97.1%) of 10-((3-(but-3-en-1-yl)-1H-inden-1-yl)(6-(tert-butoxy)hexyl)(methyl)silyl)-5,8-dimethyl-5,10-dihydroindeno[1,2-b]indole was obtained.

$^1$H NMR (500 MHz, CDCl3): −0.71, −0.23 (3H, d), 0.82 (2H, s), 1.17 (9H, s), 1.23

1.39 (7H, m), 1.51 (1H, s), 2.26 (2H, m), 2.48 (2H, m), 2.61 (2H, m), 3.25 (2H, m), 3.50 (1H, s), 3.82 (1H, s), 4.09 (3H, m), 5.03 (2H, m), 5.89 (1H, m), 7.08 (1H, s), 7.15~7.75 (11H, m)

4-2 Preparation of Metallocene Compound

A ligand was added to a 250 mL Schlenk flask dried in an oven, and dissolved in ether, and then 2.1 equivalent weights of n-BuLi solution was added, followed by lithiation until the next day. 1 equivalent weight of $ZrCl_4(THF)_2$ was taken in a glove box, and injected into a 250 mL Schlenk flask to which ether or toluene was added to prepare a suspension. The above two flasks were cooled down to −78° C., and then ligand anion was slowly added to the Zr suspension. After completion of the injection, the reaction mixture was slowly warmed up to room temperature. In this process, when successful metallation was achieved, a purple color unique to the catalyst precursor was observed. The mixture was stirred overnight and then toluene or ether in the mixture was removed to a volume of about 1/5 under vacuum/reduced pressure, and hexane of about 5 times volume of the remaining solvent was added thereto. In this regard, the reason for adding hexane is to promote crystallization because the synthesized catalyst precursor is less soluble in hexane. This hexane slurry was filtered under argon atmosphere, and a filtered solid and a filtrate were evaporated under vacuum/reduced pressure. The resulting filter cake was weighed in a glove box and sampled to identify the synthesis, yield and purity. As a metallation solvent, ether was used, and 2.5 g (30.5%) of a violet solid was obtained from 5.8 g (9.7 mmol) of the ligand.

Purity based on NMR (wt %)=90%. Mw=762.06.

$^1$H NMR (500 MHz, $CDCl_3$): 0.81 (3H, m), 1.19 (10H, m), 1.55~1.78 (10H, m), 1.97 (2H, m), 2.26 (2H, m), 2.54 (3H, s), 3.36 (2H, m), 3.94 (3H, s), 4.16 (1H, d), 4.85 (1H, m), 5.64 (1H, s), 6.53 (1H, s), 6.97 (2H, m), 7.10~7.45 (5H, m), 7.52~7.87 (4H, m)

Preparation Example of Supported Catalyst

Example 1

1-1 Drying of Support

Silica (XPO 2410 manufactured by Grace Davison Co.) was dehydrated at a temperature of 300° C. for 12 hrs under vacuum.

1-2 Preparation of Supported Catalyst 20 g of the dried silica was introduced to a glass reactor, and a toluene solution of methylaluminoxane (MAO) (aluminum (Al), 13 mmol) was added thereto, and slowly reacted under stirring at 40° C. for 1 hr. Thereafter, the reaction solution was washed with a sufficient amount of toluene to remove an unreacted aluminum compound. Next, the remaining toluene was removed at 40° C. under reduced pressure. As a result, 32 g of a methylaluminoxane-supported support was obtained. 17 wt % of aluminum was included in the resulting support.

12 g of the methylaluminoxane-supported support was injected into a glass reactor, and 70 mL of toluene was injected thereto. A toluene solution in which 1 mmol (based on zirconium) of the metallocene compound prepared in Preparation Example 1 was dissolved was added to the glass reactor, and reacted at 40° C. for 1 hr under stirring. After completion of the reaction, the solution was washed with a sufficient amount of toluene, and dried under vacuum to prepare a metallocene-supported catalyst in the form of a solid powder.

Examples 2 to 4

Each metallocene-supported catalyst was prepared in the same manner as in Example 1, except that each of the metallocene compounds of Preparation Examples 2 to 4 was used, instead of the metallocene compound of Preparation Example 1.

Example of Polyolefin Polymerization

Example 5

Each of the supported catalysts prepared in Example 1 was weighed in a dry box and introduced to a 50 mL glass bottle. The bottle was sealed with a rubber diaphragm and taken out of the dry box to prepare a catalyst for injection. Polymerization was performed in a 600 mL temperature-controllable metal alloy reactor which was equipped with a mechanical stirrer and used under a high pressure.

To this reactor, 400 mL of hexane including 1.0 mmol triethylaluminum and the supported catalyst prepared as above were introduced without contact with air. Then, polymerization was carried out for 1 hr at 80° C., while continuously providing a gaseous ethylene monomer at a pressure of 30 Kgf/cm². The polymerization was terminated by stopping the stirring and then exhausting the unreacted ethylene.

Most of the polymerization solvent was removed from the resulting polymer by filtration, and the polymer was dried in a vacuum oven at 80° C. for 4 hrs.

Examples 6 to 8

Polymerization was performed in the same manner as in Example 5, except that supported catalysts prepared in Examples 2 to 4 were used, instead of the metallocene-supported catalyst prepared in Example 1.

Supporting conditions of the respective catalysts prepared as above, catalytic activities thereof, physical properties of the resulting polymers, etc. are shown in the following Table 1.

TABLE 1

| | | Supporting recipe | | | | |
|---|---|---|---|---|---|---|
| Example No. | Supported catalyst | MAO (60° C.) mmol/g-SiO$_2$ | Met (40° C.) mmol/g-SiO$_2$ | Activity (kgPE/gCat.) | MW (g/mol) | Molecular weight distribution (PDI) |
| Example 5 | Example 1 | 8 | 0.1 | 9.3 | 520,000 | 2.4 |
| Example 6 | Example 2 | 8 | 0.1 | 9.9 | 590,000 | 2.5 |
| Example 7 | Example 3 | 8 | 0.1 | 11.3 | 443,000 | 2.6 |
| Example 8 | Example 4 | 8 | 0.1 | 14.0 | 509,000 | 2.2 |

Polymerization conditions: ethylene pressure of 40 bar, temperature of 80° C., reaction time of 60 min.

Referring to Table 1, the metallocene-supported catalyst of the present disclosure maintains high activity during olefin polymerization, even when it is supported on a support, and is able to prepare a polyolefin having a high molecular weight.

What is claimed is:

1. A metallocene compound represented by the following Chemical Formula 1:

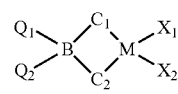

[Chemical Formula 1]

wherein M is titanium, zirconium or hafnium;

B is carbon, silicon, or germanium;

$Q_1$ and $Q_2$ are the same as or different from each other, and each independently is hydrogen, a methyl group, an ethyl group, a propyl group, an isopropyl group, an n-butyl group, a tert-butyl group, a methoxymethyl group, a tert-butoxymethyl group, a tert-butoxyhexyl group, a 1-ethoxyethyl group, a 1-methyl-1-methoxyethyl group, a tetrahydropyranyl group or a tetrahydrofuranyl group;

$X_1$ and $X_2$ are the same as or different from each other, and each is independently a halogen;

one of $C_1$ and $C_2$ is represented by the following Chemical Formula 2a, and the other is represented by the following Chemical Formula 2b:

[Chemical Formula 2a]

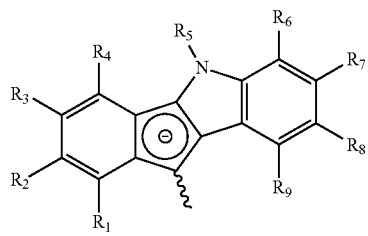

[Chemical Formula 2b]

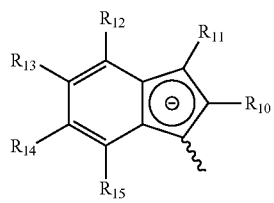

in Chemical Formula 2a, $R_1$ to $R_4$, $R_6$, $R_7$ and $R_9$ are hydrogen, and $R_5$ and $R_8$ are the same as or different from each other, and each independently is a halogen, a methyl group, an ethyl group, a propyl group, an isopropyl group, an n-butyl group, a tert-butyl group, a pentyl group, a hexyl group, a heptyl group, an octyl group, an ethylene group, a propylene group, a butenyl group, a phenyl group, a benzyl group, a naphthyl group, a methoxy group, an ethoxy group, a tert-butoxyhexyl group, a trimethylsilyl group, a triethylsilyl group, a tripropylsilyl group, a tributylsilyl group, a triisopropylsilyl group, a trimethylsilylmethyl group, or a tert-butyldimethylsilylether group;

in Chemical Formula 2b, $R_{10}$ and $R_{12}$ to $R_{15}$ are hydrogen, and $R_{11}$ is a methyl group, an ethyl group, a propyl group, an isopropyl group, an n-butyl group, a tert-butyl group, a pentyl group, a hexyl group, a heptyl group, an octyl group, an ethylene group, a propylene group, a butenyl group, a phenyl group, a benzyl group, a naphthyl group, a trimethylsilyl group, a triethylsilyl group, a tripropylsilyl group, a tributylsilyl group, a triisopropylsilyl group, a trimethylsilylmethyl group, a tert-butyldimethylsilylether group, a methoxy group, an ethoxy group, a tert-butoxyhexyl group, an aryl group, an alkylaryl group or an arylalkyl group.

2. The metallocene compound of claim 1, wherein $Q_1$ and $Q_2$ of Chemical Formula 1 are a methyl group or a tert-butoxyhexyl group.

3. The metallocene compound of claim 1, wherein the compound represented by Chemical Formula 2a is one of the following structural formulae:

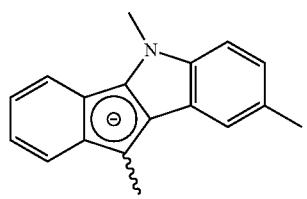

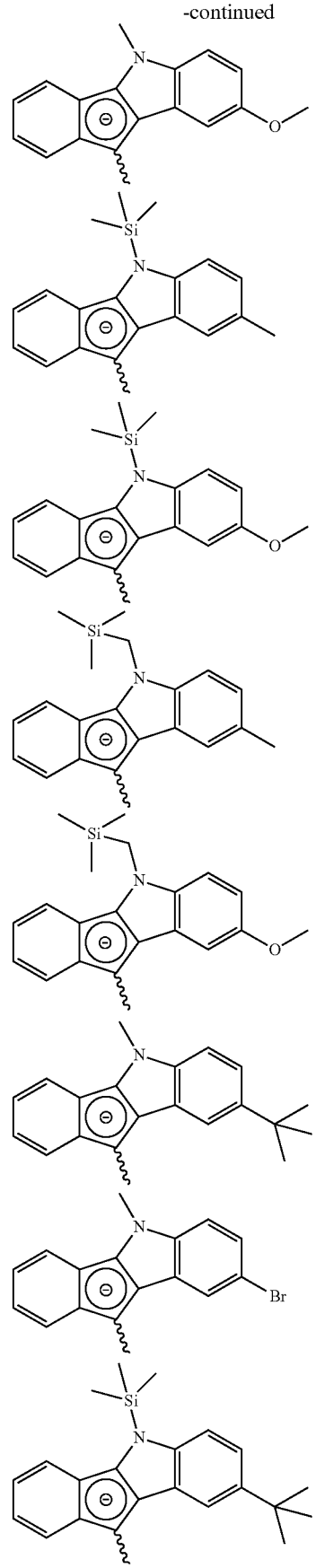

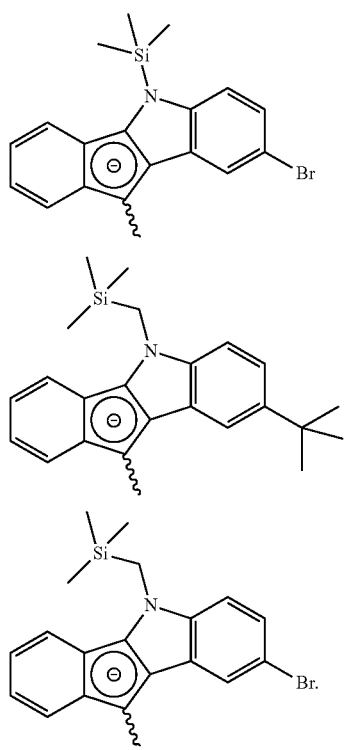
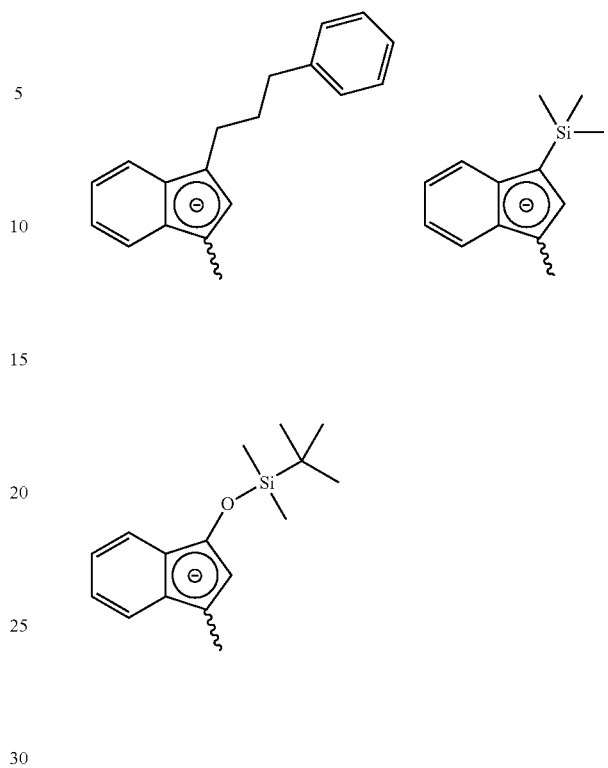
4. The metallocene compound of claim 1, wherein the compound represented by Chemical Formula 2b is one of the following structural formulae:
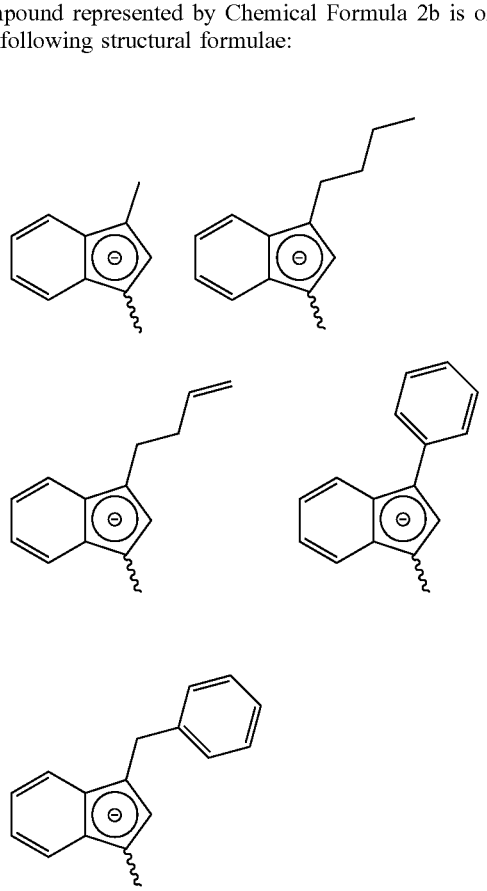
5. The metallocene compound of claim 1, wherein the compound represented by Chemical Formula 1 is one of the following structural formulae:
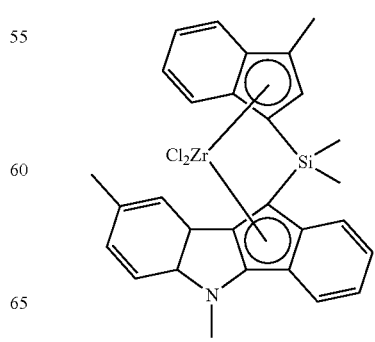

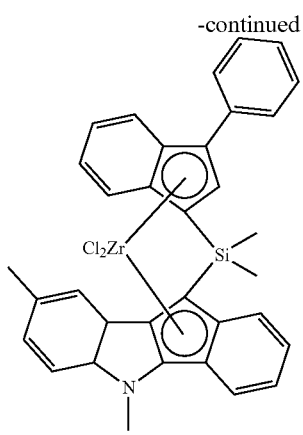
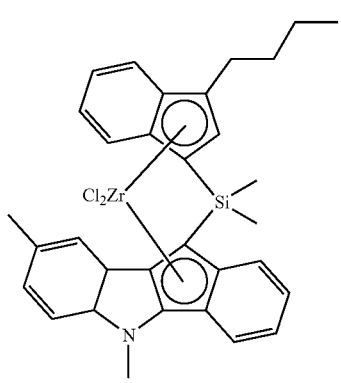
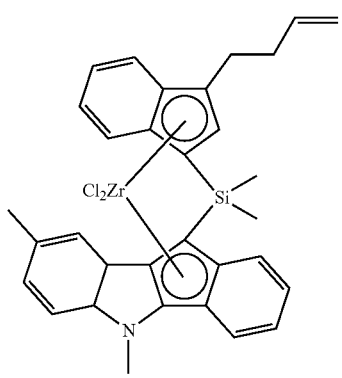
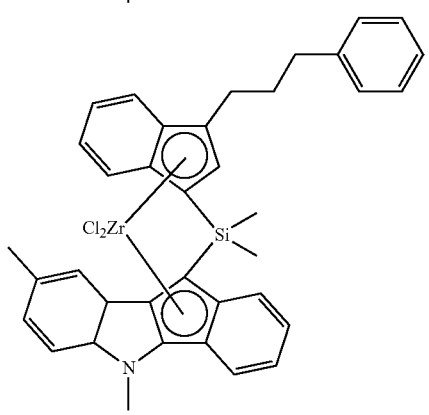
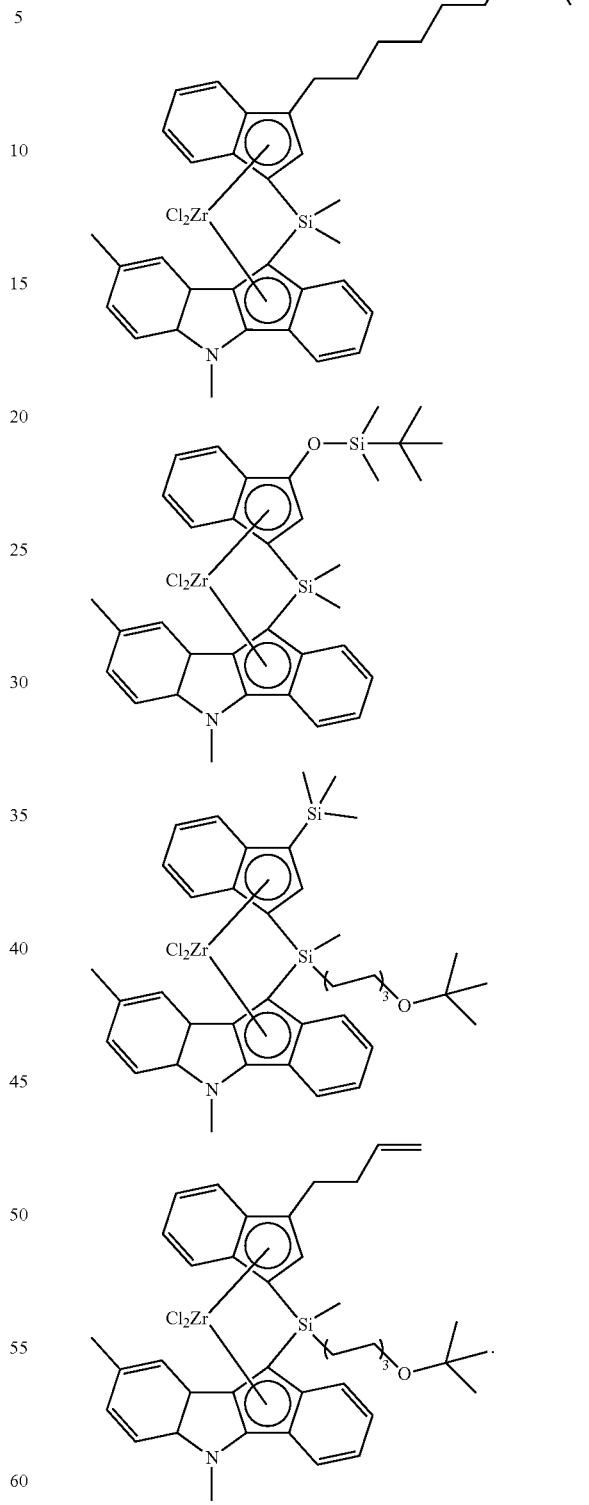
6. A metallocene-supported catalyst, comprising the metallocene compound of claim 1;
a cocatalyst compound; and
a support.

7. The metallocene-supported catalyst of claim 6, wherein the cocatalyst compound comprises one or more of compounds represented by the following Chemical Formula 3, Chemical Formula 4, and Chemical Formula 5:

—[Al(R$_{16}$)—O]$_n$—  [Chemical Formula 3]

wherein R$_{16}$s are the same as or different from each other, and each independently halogen; C1 to C20 hydrocarbon; or halogen-substituted C1 to C20 hydrocarbon; and n is an integer of 2 or more;

J(R$_{17}$)$_3$  [Chemical Formula 4]

wherein R$_{17}$s are the same as defined in Chemical Formula 3; and

J is aluminum or boron;

[E-H]$^+$[ZA$_4$]$^-$ or [E]$^+$[ZA$_4$]$^-$  [Chemical Formula 5]

wherein E is a neutral or cationic Lewis acid;

H is a hydrogen atom;

Z is a Group 13 element; and

As are the same as or different from each other, and each independently a C6 to C20 aryl group or a C1 to C20 alkyl group, of which one or more hydrogen atoms are unsubstituted or substituted with halogen, C1 to C20 hydrocarbon, alkoxy, or phenoxy.

8. The metallocene-supported catalyst of claim 6, wherein the support is one or more selected from the group consisting of silica, silica-alumina, and silica-magnesia.

9. The metallocene-supported catalyst of claim 6, wherein a weight ratio of the transition metal of the metallocene compound to the support is 1:10 to 1:1,000.

10. The metallocene-supported catalyst of claim 6, wherein a weight ratio of the cocatalyst compound to the support is 1:1 to 1:100.

11. A method of preparing a polyolefin, the method comprising polymerizing olefinic monomers in the presence of the metallocene-supported catalyst of claim 6.

12. The method of claim 11, wherein the polymerization is performed by a solution polymerization process, a slurry process, or a gas phase process.

13. The method of claim 11, wherein the olefinic monomer comprises one or more monomers selected from the group consisting of ethylene, propylene, 1-butene, 1-hexene, 1-octene, 1-pentene, 4-methyl-1-pentene, 1-heptene, 1-decene, 1-undecene, 1-dodecene, norbornene, ethylidenenorbornene, styrene, alpha-methylstyrene, and 3-chloromethylstyrene.

14. A polyolefin prepared by the preparation method of claim 11.

15. The polyolefin of claim 14, wherein a weight average molecular weight is 200,000 g/mol to 900,000 g/mol.

* * * * *